United States Patent [19]

Neubert et al.

[11] 4,204,323

[45] May 27, 1980

[54] DENTAL IMPRESSION TRAY

[75] Inventors: Hans D. Neubert, Anaheim; Larry R. Dailey, Fountain Valley; Richard S. Robinson, Anaheim, all of Calif.

[73] Assignee: NDR Associates, Anaheim Hills, Calif.

[21] Appl. No.: 834,568

[22] Filed: Sep. 19, 1977

[51] Int. Cl.² ............................................. A61C 9/00
[52] U.S. Cl. ..................................... 433/38; 433/48
[58] Field of Search ............................... 32/17, 19, 18

[56] References Cited

U.S. PATENT DOCUMENTS

| 2,703,452 | 3/1955 | Getz ......................................... 32/19 |
| 3,978,585 | 9/1976 | Holcomb .................................. 32/17 |

*Primary Examiner*—Robert Peshock
*Attorney, Agent, or Firm*—Willie Krawitz

[57] ABSTRACT

A dental tray is provided using a molded plastic. One form of tray includes buccal and lingual walls defining a series of recesses or indentations on opposed wall faces. When in use, a flexible impression support is applied to the walls and is coated with a suitable impression cement which enters the recesses and secures the impression support thereto.

After an impression has been taken, the impression support is stripped from the tray and a mold is made therefrom.

The use of recesses in the walls facilitates manufacturing of an inexpensive device of plastic using high speed, injection molding techniques.

9 Claims, 7 Drawing Figures

DENTAL IMPRESSION TRAY

BACKGROUND OF THE INVENTION

This invention relates to a molded plastic dental tray employed to obtain dental impressions.

A typical dental tray for obtaining impressions is disclosed in U.S. Pat. No. 2,583,170 to E. H. Getz, and this device has been commercialized for many years as a double bite wing tray in metal form. The Getz tray includes buccal and lingual walls joined by a connecting bar, each tray being manufactured in sections which are perforated by machining and then joined together. The manufacturing operation is expensive since each tray must be perforated and then brazed together in a joining operation. Furthermore, all edges must be smoothed to eliminate any projecting metal portions which could injure a patient's mouth while in use. Overall, the Getz type tray is an expensive device.

If it were possible to produce a double bite wing tray in a molded plastic form, a considerable saving could be effected both in terms of a simpler mold and also with a faster production run. However, forming a large number of perforations in a molded plastic dental tray which could perform the same function as the Getz type tray is costly in terms of mold expenses. Nevertheless, a molded plastic dental tray which is equivalent to the Getz type metal tray is desired. Preferably, such a molded plastic dental tray would be formed using standard injection molding techniques to attain high production rates and a corresponding decrease in unit costs.

In addition to the Getz tray, many other forms of perforated dental impression trays have been used in the past, the perforations functioning to lock an impression support material thereto. However, it is physically difficult to clean the impression material from the perforations, and if a cleaning compound is employed, this represents an added expense and generally requires an extended immersion period.

THE INVENTION

According to the invention, a molded plastic dental tray is provided having a plurality of recesses or cavities disposed on retaining walls of the tray, an impression substrate is fitted onto the walls, and an impression material is coated onto the tray and substrate; when in use, the impression material enters the recesses and locks the substrate in place. A dental tray which has been provided with impression retaining recesses functions equally as well as perforated tray and is less expensive to maufacture. In addition, the recess surfaces tend to be relatively exposed to the bristles of a cleaning brush and are readily cleaned compared to a perforated surface.

In a preferred embodiment, an injection molded plastic dental tray is provided having an upper lingual and lower buccal wall defining opposed faces; spacing means are provided to separate and join the upper and lower walls. A plurality of recesses or cavities are disposed on the surface of the opposed faces and means are provided on the dental tray to secure a flexible support adapted to obtain a dental impression thereon.

The recesses are made large enough so that sufficient dental impression material will enter and lock an impression substrate thereto. In the case of a double bite wing tray, the total area of the recesses along a wall surface is typically about $0.55 \pm 0.05$ in.$^2$ over a total area of opposed buccal and lingual walls of about $6 \pm 0.6$ in.$^2$. The height of a recess varies from about 0.09–0.375 inches and has an average height of about 0.2 inches.

Plastic materials which may be used for the injection molding of the dental trays include: polypropylene, nylon, polyester, etc. Polyoxetanes, polycarbonates, rubbers, polyurethanes, etc., also may be employed for a plastic molding process.

DESCRIPTION OF THE PREFERRED EMBODIMENT

Figure 1:
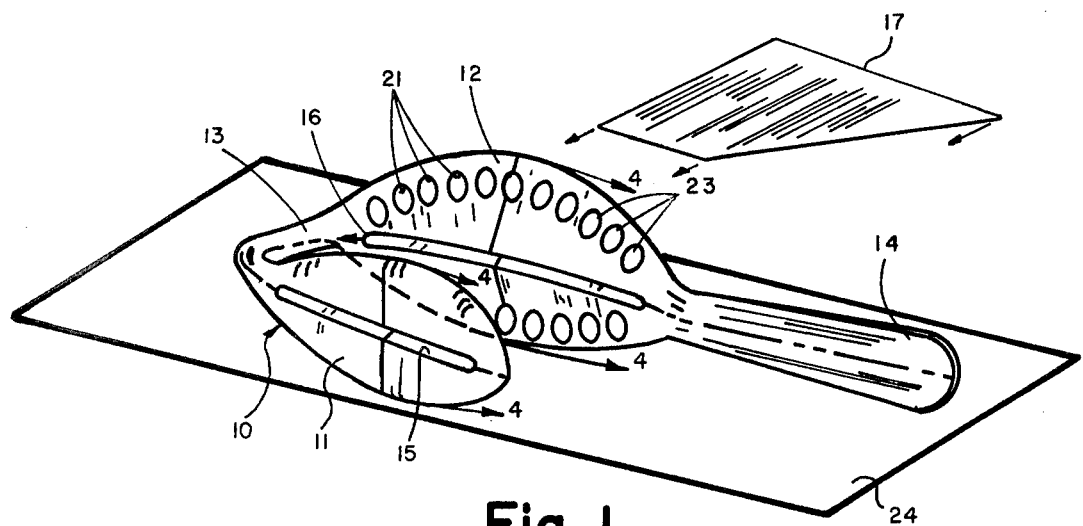
FIG. 1 is a perspective view of a double bite wing tray according to the invention.
Figure 4:
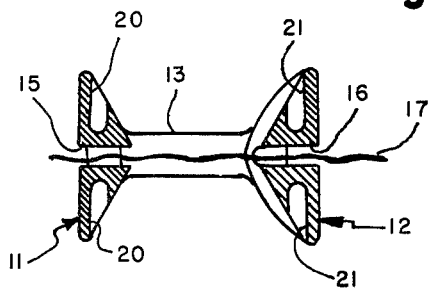
FIG. 4 is a section of the impression tray taken along lines 4—4 of FIG. 1 showing an impression substrate in place.

One form of the invention is shown in FIG. 1 which illustrates a dental tray 10 having spaced upper lingual and lower buccal walls 11, 12 respectively joined together by a spacing member 13. The lower wall is provided with a handle 14. Slits 15, 16 are defined by the upper and lower walls 11, 12 respectively, the slits being adapted to receive and retain a paper occlusal insert 17 which is fed into the tray in the direction shown by the arrows. A plurality of recesses 20, 21 are provided on opposed sides 22, 23 of the upper and lower walls 11, 12 respectively.

The recesses 20, 21 define central longitudinal axes 23 which preferably are oriented approximately orthogonal to a plane 24 that passes through and along each slit 15, 16 and which bisects the tray as shown. This orientation enables the most efficient bond between a recess and the impression material to be established. Furthermore, this orientation permits the mold to be removed from the product (i.e. the tray) in the same direction the product is being ejected from the injection molding process. Hence, less time is required to remove the mold from a product tray and this speeds up the production rate considerably.

Figure 5:
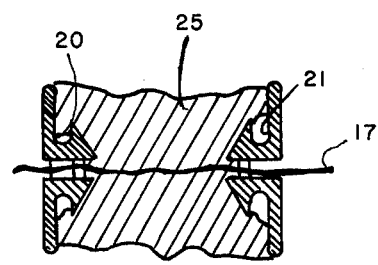
FIG. 5 is a view of FIG. 4 showing the impression tray and impression substrate coated with an impression material; and, FIGS. 6 and 7 show two views of the impression tray of FIG. 5 in use when obtaining a dental impression.
Figure 7:
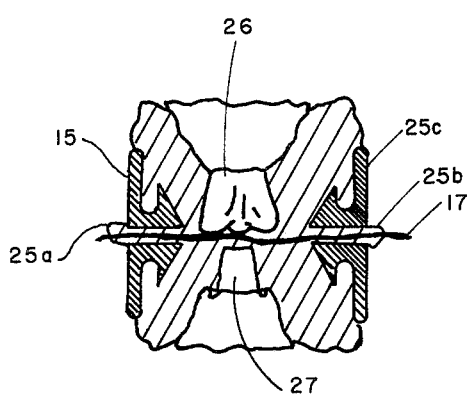
Figure 6:
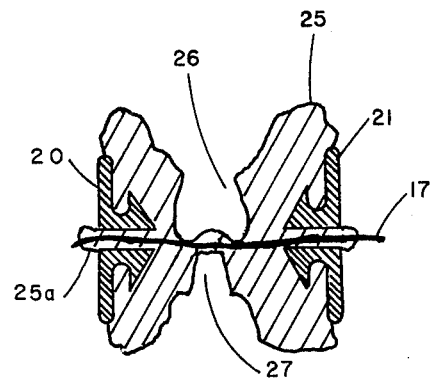
Figure 2:
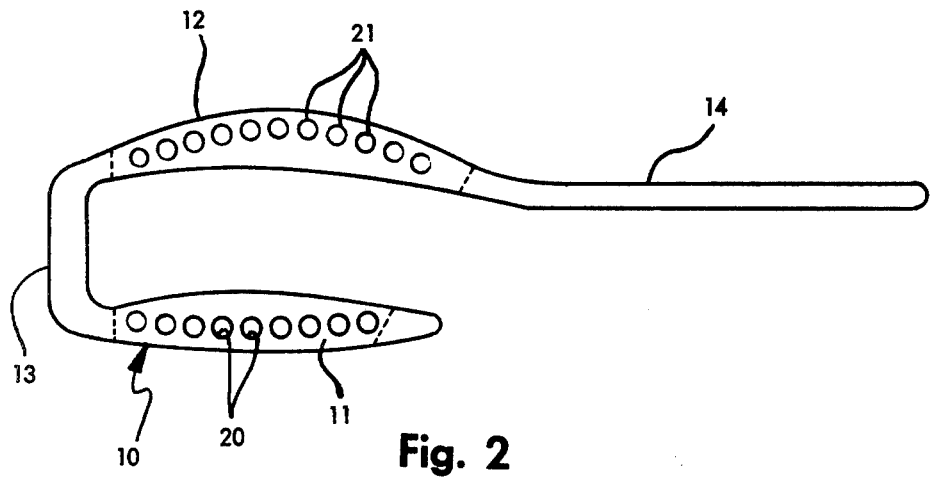
FIG. 2 is a side elevation view of the dental impression tray in axial section.
Figure 3:
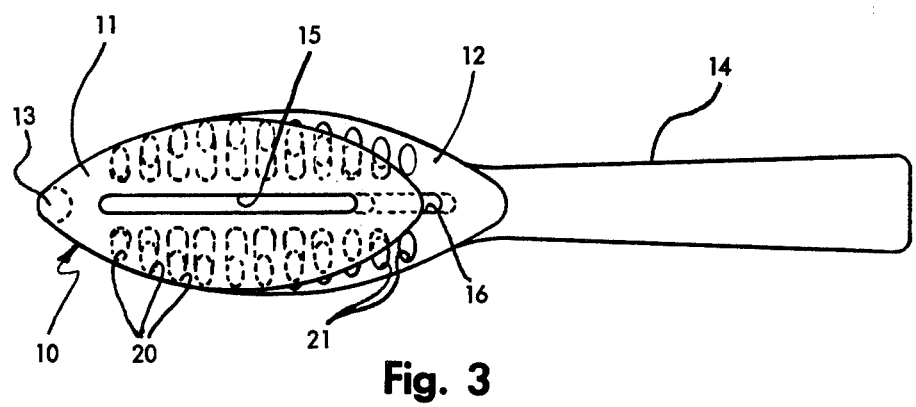
FIG. 3 is a plan view of the impression tray.

In operation, an occlusal insert 17 in the form of a flexible paper substrate is inserted into the tray and impression material such as a rubber cement, etc., is applied to the tray walls and the substrate as shown in FIG. 5. At this time, the impression material 25 has entered the recesses 20, 21 only slightly and has not exuded beyond the slits 15, 16. The dental tray is then inserted into a patient's mouth and the patient commences to bite down on the flexible substrate with a normal tooth 26 and opposed contoured tooth 27 which has been prepared for, say, a crown. As shown in FIG. 6, impression material 25 will then be pressured so as to partly fill the recesses 20, 21; the impression material also will be forced out the slits 15, 16 to form ridges 25a, 25b. When the opposed teeth 26, 27 are closed almost completely together as shown in FIG. 7, the impression material will be completely pressured into the recesses 20, 21 to form beads 25c therein; the beads function to lock the occlusal insert 17 in place on the lingual and buccal walls 11, 12 when an impression is being taken. After the impression material has set, the dental tray is removed from the patient's mouth and the insert 17 is stripped from the tray along with the beads of impression material which were pressured into the recesses. Consequently, there is far less, if any, impression material retained in the recesses that requires removal by cleaning.

Various types of impression trays for dental (including oral) purposes may be produced according to the invention and some are disclosed in U.S. Pat. Nos. 3,468,029 and 4,003,132; these patents disclose dental trays employing impression substrates. The present invention enables the perforations in these trays to be replaced by recesses because the bond which is formed between the impression material and the recesses is equivalent to the bond formed with a perforated tray. Furthermore, a tray having surface recesses is structurally more sound than a perforated tray of the same material and hence will last longer.

We claim:

1. An integral dental impression tray formed from a plastic injection molding process comprising:
   a. spaced-apart buccal and lingual retaining walls defining opposed wall portions;
   b. a plurality of recesses disposed on the opposed wall portions;
   c. a spacing member for connecting the buccal and lingual walls, the tray defining a central longitudinal plane of symmetry through the spacing member and centrally through both walls, and the recesses defining central longitudinal axes disposed about orthogonally to the symmetry plane and outwardly therefrom; and,
   d. central slits disposed medially along the buccal and lingual walls, the plane of symmetry passing through each slit, to secure a flexible sheet support for obtaining a dental impression thereon;
   the recesses being adapted to engage with beads of the dental impression material, thereby locking the flexible support and the tray together while a dental impression is being made, and to permit stripping of the flexible support from the tray.

2. The dental impression tray of claim 1 in which the plastic is selected from the class consisting of: polypropylene, nylon, polyester, polyoxetane, polycarbonate, polyurethane and rubber.

3. The dental impression tray of claim 1 in which the dental impression on the flexible support comprises a rubber cement.

4. The dental impression tray of claim 1 providing a total area of opposed buccal and lingual walls of about 6 in.$^2$, and the total area of the recesses is about 0.55 in.$^2$.

5. The dental impression tray of claim 1 in which the total area of the recesses is about 0.55 in.$^2$, and the height of a recess varies from about 0.09–0.35 inches.

6. The dental impression tray of claim 1 in which the total area of the opposed buccal and lingual walls is about 6 in.$^2$, and the total area of the recesses is about 0.55 in.$^2$, and the height of a recess varies from about 0.09–0.35 inches.

7. The dental tray of claim 1 in which the tray is removed from its associated mold in the same direction as it is ejected from the injection molding process.

8. A method of producing a dental impression from an integral dental impression tray formed from a plastic injection molding process, the tray including:
   a. spaced-apart buccal and lingual retaining walls defining opposed wall portions;
   b. a plurality of recesses disposed on the opposed wall portions;
   c. a spacing member for connecting the buccal and lingual walls, the tray defining a central longitudinal plane of symmetry through the spacing member and centrally through both walls, and the recesses defining central longitudinal axes disposed about orthogonally to the symmetry plane and outwardly therefrom; and,
   d. central slits disposed medially along the buccal and lingual walls, the plane of symmetry passing through each slit, to secure a flexible sheet support for obtaining a dental impression thereon;
   the recesses being adapted to engage with beads of the dental impression material, thereby locking the flexible support and the tray together while a dental impression is being made, and to permit stripping of the flexible support from the tray;
   the steps comprising:
   A. securing the occlusal insert within the slits;
   B. applying an impression material to the tray wall and occlusal insert;
   C. forming a dental impression on the occlusal insert, the recesses being adapted to engage with beads of dental impression material, thereby locking the tray and the occlusal insert while a dental impression is being made; and,
   D. removing the occlusal insert by stripping the impression from the recesses.

9. The method claim 8 in which the tray is removed from its associated mold in the same direction as it is ejected from the injection molding process.

* * * * *